United States Patent [19]

Finney

[11] Patent Number: 4,573,985

[45] Date of Patent: Mar. 4, 1986

[54] URINARY COLLECTION METHOD AND DEVICE

[75] Inventor: Roy P. Finney, Tampa, Fla.

[73] Assignee: Medical Engineering Corp., Racine, Wis.

[21] Appl. No.: 568,745

[22] Filed: Jan. 6, 1984

Related U.S. Application Data

[63] Continuation-in-part of Ser. No. 150,231, May 15, 1980, Pat. No. 4,318,396, and a continuation-in-part of Ser. No. 266,455, May 22, 1981, abandoned, and a continuation-in-part of Ser. No. 328,827, Dec. 9, 1981, Pat. No. 4,411,261, and a continuation-in-part of Ser. No. 478,449, Mar. 24, 1983, Pat. No. 4,532,920.

[51] Int. Cl.⁴ ............................................. A61F 5/44
[52] U.S. Cl. ..................................... 604/349; 128/79
[58] Field of Search ..................... 128/79, 344; 3/1; 604/349

[56] References Cited

U.S. PATENT DOCUMENTS

| | | | |
|---|---|---|---|
| 4,009,711 | 3/1977 | Uson | 3/1 |
| 4,019,499 | 4/1977 | Fitzgerald | 128/1 R |
| 4,066,073 | 1/1978 | Finney et al. | 128/79 |
| 4,235,227 | 11/1980 | Yamanaka | 128/79 |
| 4,318,396 | 3/1982 | Finney | 128/79 |
| 4,381,767 | 5/1983 | Finney | 128/79 |
| 4,387,705 | 6/1983 | Finney | 128/1 R |

Primary Examiner—Dalton L. Truluck
Attorney, Agent, or Firm—Quarles & Brady

[57] ABSTRACT

The elastic sheath of a urinary collection device is more securely retained in place upon the penis of an incontinent patient by modifying the patient's penis by making an incision in the penis, implanting penile implants having expansible chambers and a self sealing tip in the corpora cavernosa of the penis, closing the incision and then periodically filling the chambers with fluid introduced through a cannula extending through the glans of the penis and the self sealing tip. The periodic addition of fluid to the chambers causes them to gradually expand and stretch the penile tissue until the penis is larger and firmer and will more securely retain the elastic sheath of the collection device. The implants are especially useful for patients having spinal cord injuries because the implants are soft and not rigid even when filled and therefore they are less likely to erode through the skin of the penis or the urethra.

2 Claims, 4 Drawing Figures

URINARY COLLECTION METHOD AND DEVICE

RELATED APPLICATION

The present application is a continuation-in-part of my earlier patent applications Ser. No. 150,231 filed May 15, 1980, now U.S. Pat. No. 4,318,396, Ser. No. 266,455 filed May 22, 1981, now abandoned, Ser. No. 328,827 filed Dec. 9, 1981, now U.S. Pat. No. 4,411,261 and Ser. No. 478,449 filed Mar. 24, 1983 now U.S. Pat. No. 4,532,920.

FIELD OF THE INVENTION

The present invention relates to the collection of urine and more particularly to a method of modifying the penis of an incontinent patient to more securely retain the flexible sheath of a urinary collection device in place and to penile implants for use in that method.

DESCRIPTION OF THE PRIOR ART

Incontinent male patients, such as those suffering from spinal cord injuries, often wear devices for the collection of urine. The urinary collection device most widely used with incontinent male patients is commonly called a "Texas Catheter" and it consists of a flexible condom-like sheath which is secured to the patient's penis and a tubular member which connects the condom-like device to a suitable urine receptacle. A device of this type is shown in the Rogers et al U.S. Pat. No. 3,835,857, granted Sept. 17, 1974.

One of the problems involved in the use of the "Texas Catheter" is that the sheath which depends upon its elasticity to stay in place can be accidently removed quite easily from the patient's penis without the patient being aware of its removal. This is especially a problem where the patient's penis is small and soft. Another Rogers et al patent, U.S. Pat. No. 3,863,638, discloses a liner which has an adhesive coating which clings to the penis and which is designed to retain the elastic sheath on the penis. Still another patent relating to a sheath liner useful for this purpose is U.S. Pat. No. 4,187,851.

Although the use of an adhesive coated sheath liner is an improvement on the use of the sheath itself in preventing accidental removal, it is not without disadvantages. For example, the liner normally has to be either placed on or removed from the penis of the patient by a person other than the patient. In addition, the liner and its adhesive layer can cause tissue irritation. Obviously, therefore, a need still exists for an improved means or method for securely attaching the sheath of a "Texas Catheter" to the penis of an incontinent male patient.

In U.S. Pat. No. 4,381,767 and U.S. Pat. No. 4,387,705, I disclosed novel penile implants for retaining the sheath of a urinary collection device upon the penis of an incontinent male. Each of the implants included a D-shaped ring of soft but firm biocompatible material which was implanted around the penile shaft beneath the penile skin at the distal end of the patient's penis. The ring formed a protuberance which increased the external diameter of the penis and helped to retain the flexible elastic sheath in place.

I have now discovered an alternative method for retaining the elastic sheath in place and an implant for use in that method.

SUMMARY OF THE PRESENT INVENTION

It is an object of the present inventon to disclose a novel method of modifying the penis of an incontinent patient so that the sheath of a urinary collection device is more securely retained upon the penis without the use of liners and in a manner which is more acceptable to the patient.

It is another object of the present invention to disclose penile implants which when surgically implanted help retain the flexible, elastic sheath of a urinary collection device in place.

In the method of the present invention, the penis of a patient is modified by implanting a pair of inflatable implants in the penis. One implant is positioned in each of the corpora cavernosa of the penis. Expansible chambers in the implants are then filled over an extended period of time by adding fluid to the chambers with a hollow needle or cannula which extends through the glans of the penis and the self-sealing tip of the implant. The chambers and the penile tissue are thus gradually stretched and expanded until the penis is larger and firmer but it is still flexible enough to bend without discomfort to the patient. The thus modified penis helps to securely retain the elastic sheath of the urinary collection device in place.

The penile implants of the present invention are soft, flexible elongated cylinders which preferably have a short stem portion of relatively stiff material for implanting in the root end of a corpus cavernosum to anchor the implant, and a flexible, inflatable, expansible, intermediate portion and a self-sealing tip which are implanted in the portion of the corpus cavernosum in the pendulous penis. The implants resemble the penile implants used for correcting erectile impotence, but they are much softer.

Incontinent patients which have spinal cord injuries usually have no sensation of pain or any other sensation in the penis. When a semi-rigid rod type penile implant of the type disclosed in my U.S. Pat. No. 4,066,073 is implanted in such a patient, the implants do help to keep the elastic sheath of a collection device in place, but the implants are relatively stiff and often erode through the skin or urethra and have to be removed. The stiff implants usually do not erode in a man with normal sensation because he can feel the discomfort on the end of the penis from pressure caused by clothes and the like, and he can make adjustments to relieve that pressure. When the soft implants of the present invention are implanted in the penis of a patient having a spinal cord injury the penis can move away from pressure and there is less possibility of erosion.

The above and other objects and advantages of the invention will become apparent to those skilled in the art from the description and the drawings which follow:

DESCRIPTION OF THE PREFERRED EMBODIMENT

Figure 1:
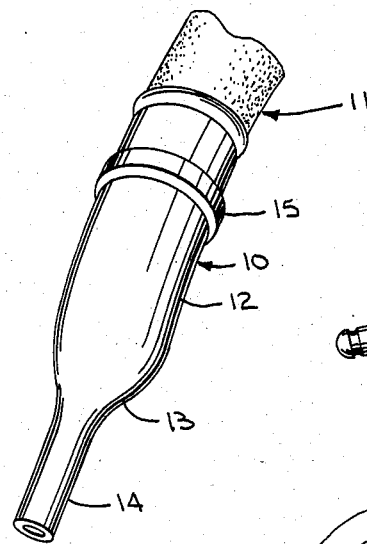
FIG. 1 is a perspective view of a penis with the implants of the present invention surgically implanted therein and a sheath of a urinary collection device in place.

Referring to FIG. 1, an elastic sheath 10 of a urinary collection device is shown positioned upon a penis 11. The sheath 10 has a body portion 12 joined to a conical funnel-like section 13 which terminates in a tube 14 which leads to a urine receptacle (not shown). The body portion 12 is of thin elastic material, such as latex rubber, which is capable of being rolled upon itself and then unrolled onto the penis 11. Normally, the elasticity of the material of the body portion 12 will keep the sheath on the penis. However, for extra security, an elastic band 15, may be positioned overlying the body portion of the sheath 10 at a point behind the glans to insure that the sheath 10 will not be accidentally removed.

Figure 2:
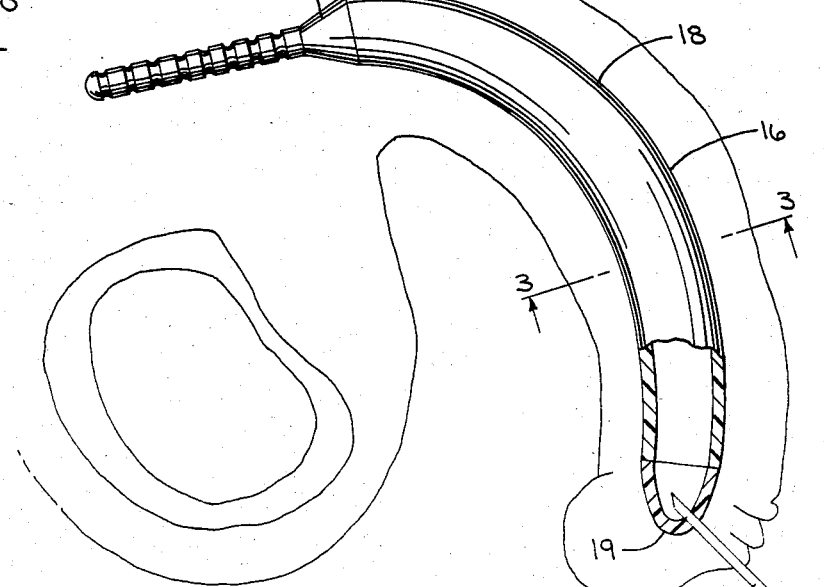
FIG. 2 is a sectional view of a penis with the implants surgically implanted therein but without the sheath.
Figure 3:
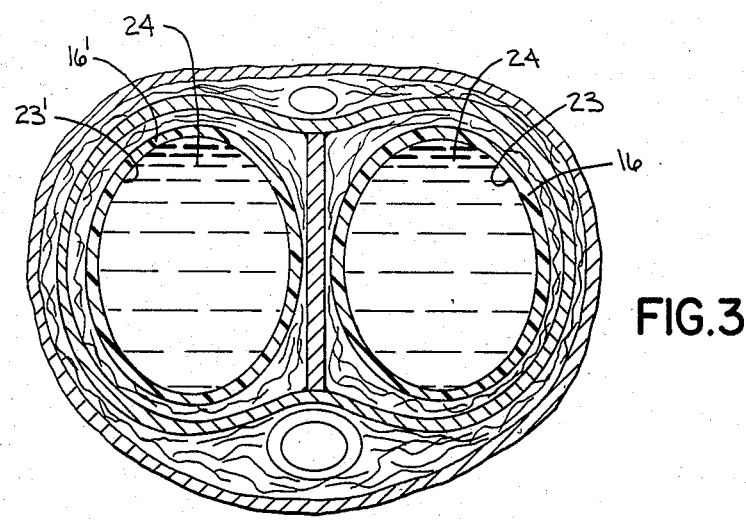
FIG. 3 is a sectional view taken along lines 3—3 in FIG. 2.

As seen in FIGS. 2 and 3, the penile implants 16, 16' are implanted in the corpora cavernosum of the penis 11.

Figure 4:
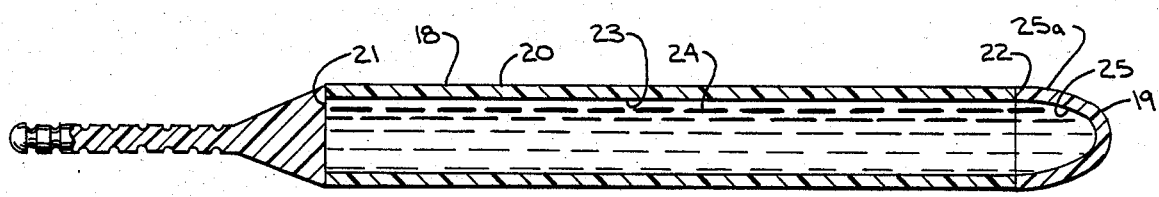
FIG. 4 is a sectional view of the preferred embodiment of the implant of the present invention.

In FIGS. 2 and 4, it can be seen that the implant 16, which is identical to implant 16', has a short, proximal stem 17 of relatively stiff material, a soft flexible expansible intermediate portion 18 and a self sealing conical tip 19. As seen in FIG. 2, the stem 17 is implanted in the root end of the corpus cavernosum to support and anchor the implant and the longer intermediate portion 18 and the tip 19 are implanted in the portion of the corpus cavernosum in the pendulous penis.

Turning to FIG. 4, it can be seen that the intermediate portion 18 of the implant comprises a flexible, elastic sleeve 20 which is sealed in a fluid-tight manner at its respective ends 21 and 22 to the inner end of stem 17 and the inner end of the tip 19 to form a cylindrical inflatable expansible chamber 23 which contains fluid 24. The seals between the ends 21 and 22 of the sleeve 20 and the stem 17 and tip 19 are preferably made with a suitable silicone adhesive.

Still referring to FIG. 4, it can be seen that the tip 19 of the implant 16 is hollow and that it contains a cavity 25 which communicates with the chamber 23. The wall 25a of the cavity 25 is of a resealable material and it serves as a self-sealing valve by which the chamber 23 can be filled with inflating fluid 24 to increase the length and girth of the penis. The chambers 23, 23' of the implants 16, 16' are preferably partially filled with a fluid, such as saline, prior to implanting and then further filled until the penis reaches the desired girth, length and firmness by periodically injecting more fluid into each of the chambers individually via a hollow cannula or needle 26 and syringe 27 as seen in FIG. 2. The needle 26 is inserted through the glans of the penis, through the resealable wall 25a into the chamber 23. When the needle is removed, the resealable wall 25a seals to retain the fluid 24 in the chamber 23. By periodically adding small increments of fluid to the chambers over an extended period of time, the tissue of the penis can be gradually stretched until the penis is a desired size with a minimum of pain and discomfort to the patient. The chambers 23, 23' are filled until they contain about 20 cc to about 30 cc of fluid and the penis assumes a firmness which is greater than that of the flaccid penis but not as firm as in the erectile state. Preferably the pressure in the chamber 23, 23' will be from about 50 cm to about 400 cm of water and preferably less than about 300 cm of water. In this condition the penis can be bent without discomfort and will securely retain the elastic sheath 10.

In the foregoing description, the proximal stem 17 of the implant 16 has been described as being stiff whereas the intermediate portion 18 has been described as being relatively soft and flexible. While the term "stiff" has been used to describe the desired physical properties of the material of the rod, a more precise and technical term is flexural modulus, which is the ratio of applied force to resulting deflection. However, most tables of properties do not describe the stiffness properties of rubber or rubberlike material. However, they do list related properties such as hardness.

Hardness is measured by a durometer such as a Shore A durometer which ascertains the depth of penetration of a specific indentor into a specimen under specified conditions. A scale is chosen so that 9 represents a material showing no measurable resistance to indentation and 100 represents a material showing no measurable indentation.

In the preferred embodiment of the invention, the proximal stem 17 of the implant 16 has a Shore hardness of about 70, and the material has sufficient tensile strength for its intended use. Although a material of the described properties is preferred, any material which performs satisfactorily under conditions of use can be employed.

The resealable tip 19 through which pressurizing fluid can be added to the chamber 23 also may take other forms than that illustrated. For example, the tip could contain a port which can be closed and reopened. The preferred material for the resealable tip is a silicone rubber material similar to that disclosed in U.S. Pat. No. 3,919,724.

The sleeve 20 is made of an elastomer such as silicone rubber which expands as the chambers 23, 23' are filled thus allowing the penis to become longer and larger. Preferably, the material of the sleeve may be an elastomer coated fabric which will expand only to a limited predetermined extent so that the penis will attain the desired size and firmness without the tunica albuginea being damaged.

The preferred method of implantation of the implants 16, 16' is through a penile shaft or penoscrotal incision and then incisions into each of the corpora. After appropriate incisions, the corpus cavernosum is dilated distally and proximally to accept the implant. The appropriate anatomical measurements are made to insure that the proximal stem 17 of the implant will be positioned at the base of the penis below the pelvic bone. Implants of the appropriate length are selected and the distal portions which consist of the intermediate portions 18 and the tips 19 are inserted into the corpora cavernosa of the pendulous penis. The proximal stem 17 of each implant may then be cut to the appropriate length, positioned in the root end of the corpus and the incisions closed.

It will be readily apparent to those skilled in the art that a variety of changes and modifications might be made without departing from the spirit and scope of the invention. Therefore, the scope of the invention is not to be limited except by the claims which follow:

I claim:

1. A method of modifying the penis of an incontinent patient so that an elastic sheath of a urinary collection device can be securely retained thereon, which method comprises making an incision in the penis, implanting into each of the corpora cavernosa of the penis a generally cylindrical penile implant having an expansible inflatable chamber and a self sealing means for filling such chamber, closing the incision, periodically injecting fluid into said chamber through said self sealing means via a cannula to stretch and expand the chamber and the penis until the penis is large enough and firm enough to securely retain the elastic sheath of a urinary collection device but still flexible enough to bend without discomfort to the patient and then placing an elastic urinary collection sheath upon the thus modified penis.

2. The method of claim 1 in which a rubber band is placed over the elastic sheath upon the thus modified penis.

* * * * *